United States Patent [19]

Unger et al.

[11] 4,438,770

[45] Mar. 27, 1984

[54] SKIN INCISING DEVICE

[75] Inventors: Hans P. O. Unger, Värtavägen 35, 115 29 Stockholm; Johan E. H. Westberg, Rödstuguvägen 14, 181 31 Lidingö, both of Sweden

[73] Assignees: Hans Peter Olof Unger; Johan Eric Hayden Westberg, both of Sweden

[21] Appl. No.: 406,050

[22] Filed: Aug. 6, 1982

Related U.S. Application Data

[63] Continuation of Ser. No. 132,409, Mar. 21, 1980, abandoned, which is a continuation-in-part of Ser. No. 945,099, Sep. 22, 1978.

[30] Foreign Application Priority Data

Mar. 23, 1979 [SE] Sweden .............................. 7902628

[51] Int. Cl.³ .............................................. A61B 17/32
[52] U.S. Cl. ..................................... 128/637; 128/314; 128/305
[58] Field of Search ............... 128/314, 315, 333, 637, 128/305, 303 R; 604/22; 30/124, 367, 272, 282, 283, 286, 289

[56] References Cited

U.S. PATENT DOCUMENTS

| 2,092,812 | 9/1937 | Nemzek | 128/314 |
| 3,010,455 | 11/1961 | Cooper | 128/305 X |
| 3,659,608 | 5/1972 | Perry | 128/314 |

OTHER PUBLICATIONS

General Diagnostics Brochure (Feb. 1977).

Primary Examiner—Michael H. Thaler
Attorney, Agent, or Firm—Hill, Van Santen, Steadman & Simpson

[57] ABSTRACT

A device for making skin incisions for bleeding time determinations in accordance with Ivy's method has a cutter guide on which an incising cutter is movable from a retracted position to an advanced position under the action of spring bias. A base surface adapted to be pressed against the patient's skin has a depression of a length corresponding to the desired length of the skin incision. A slot in the base surface extends across the depression and accommodates the tip of the cutter. When the cutter is released from the retracted position the spring bias displaces it along the slot and as it traverses the depression it makes a skin incision of predetermined constant depth.

10 Claims, 13 Drawing Figures

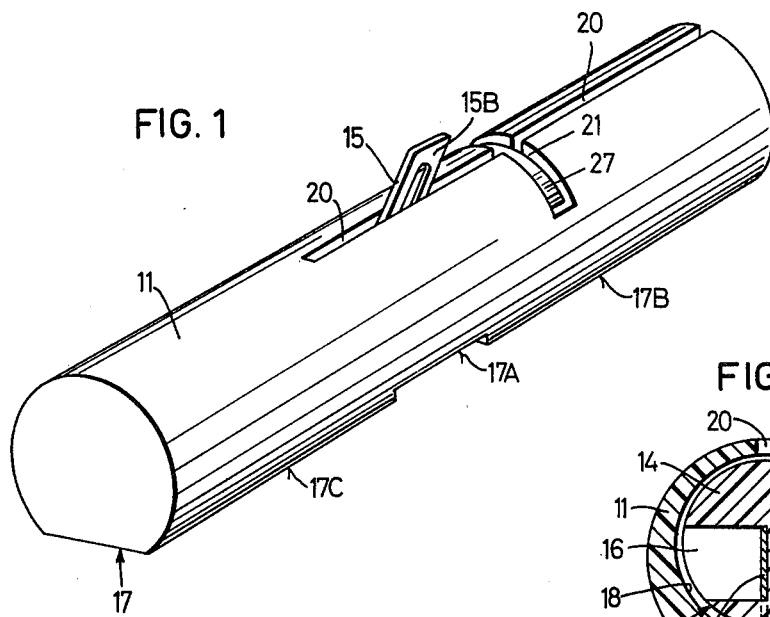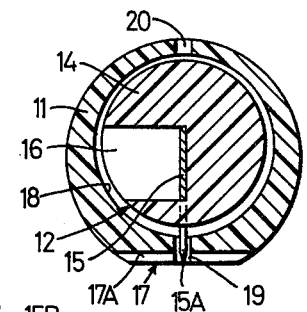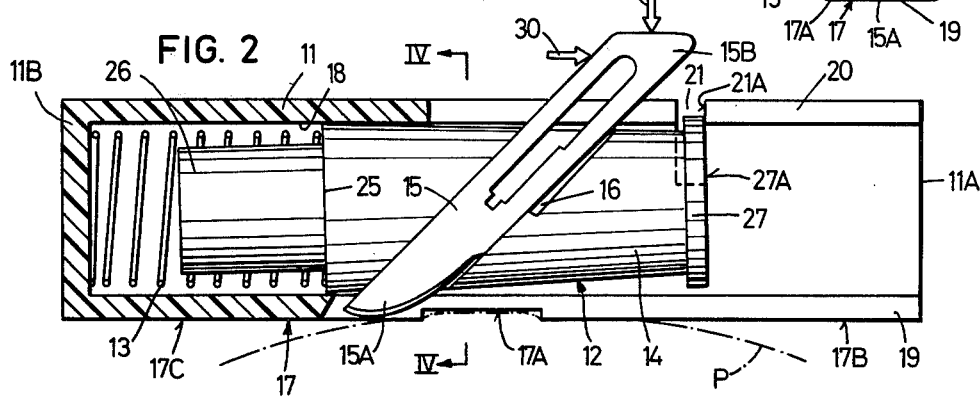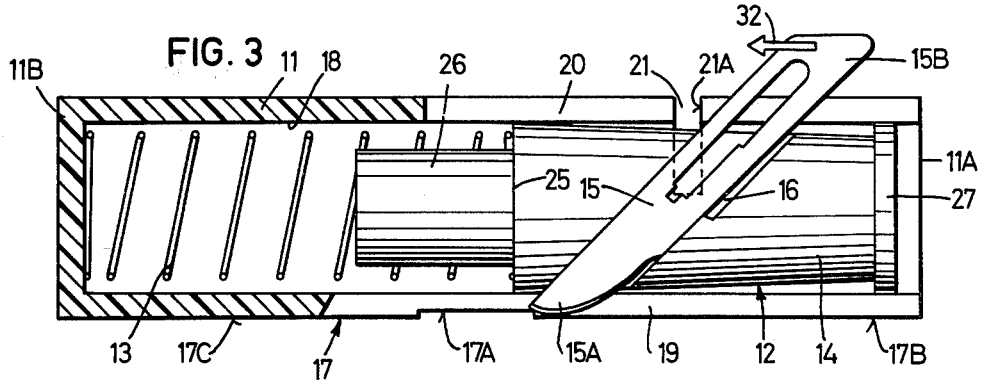

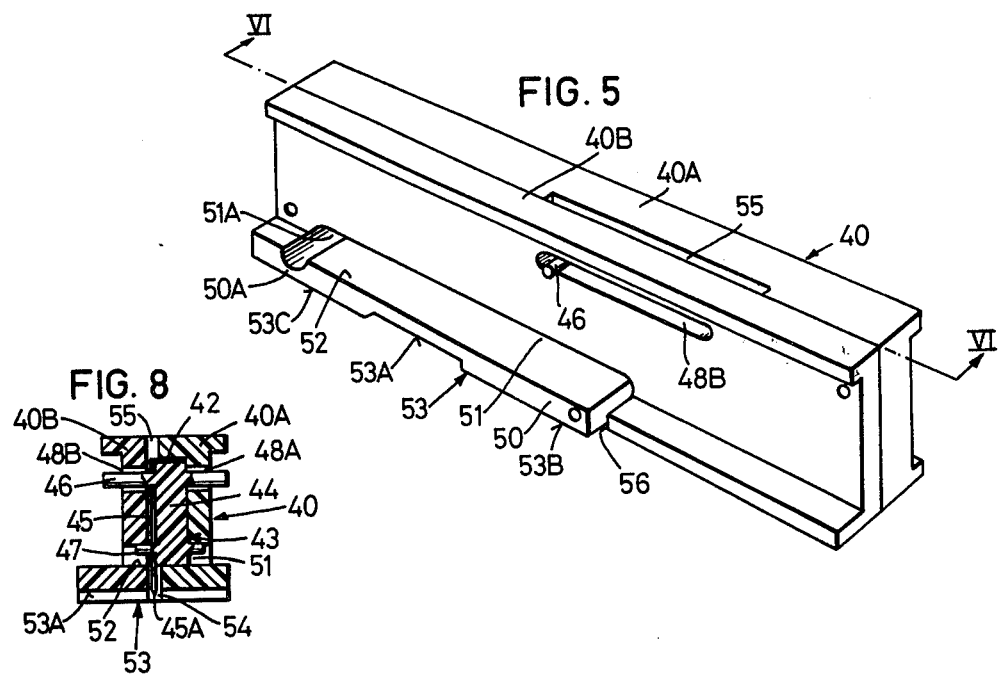
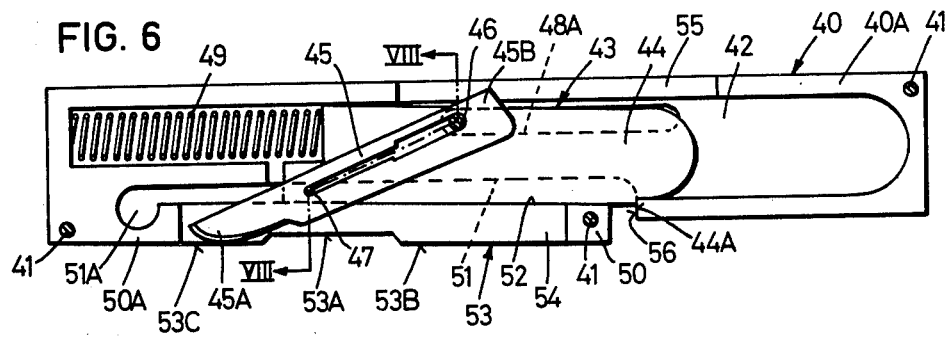
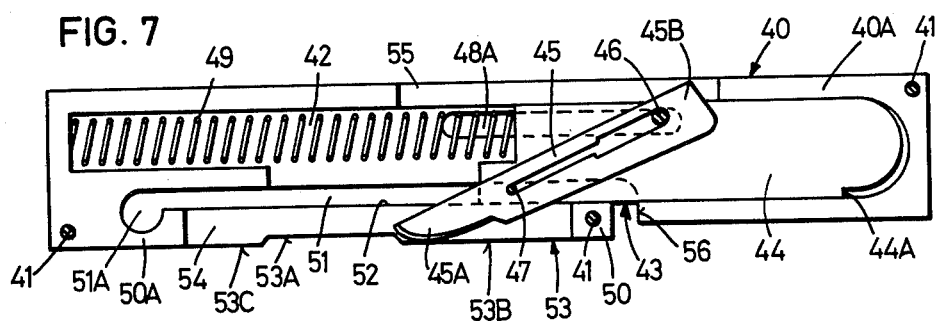

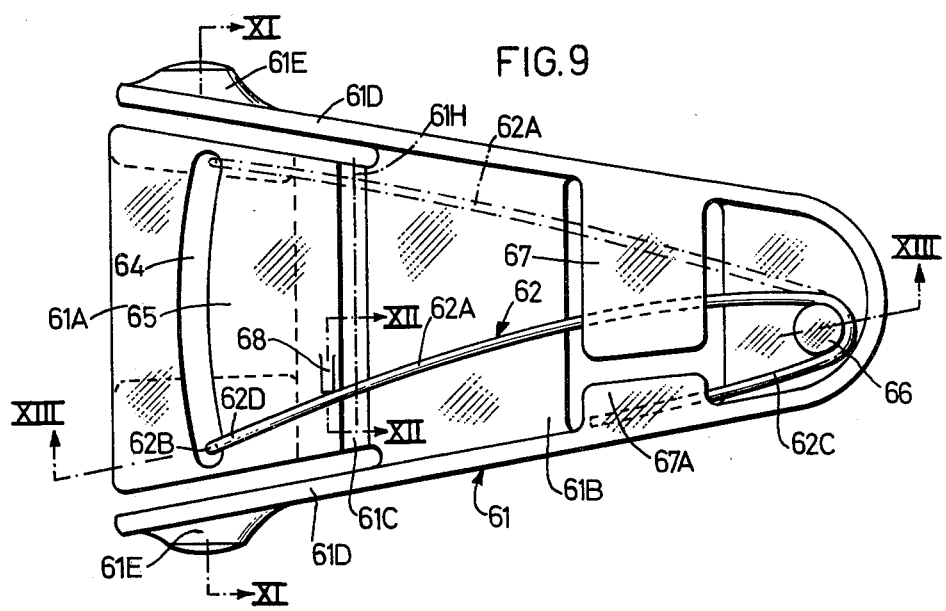
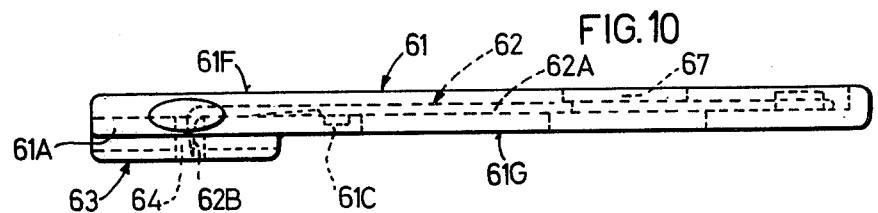
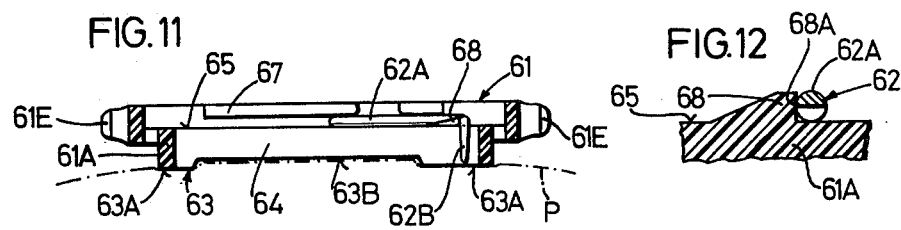
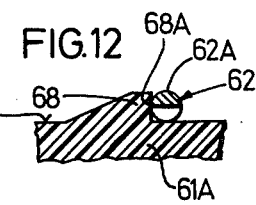
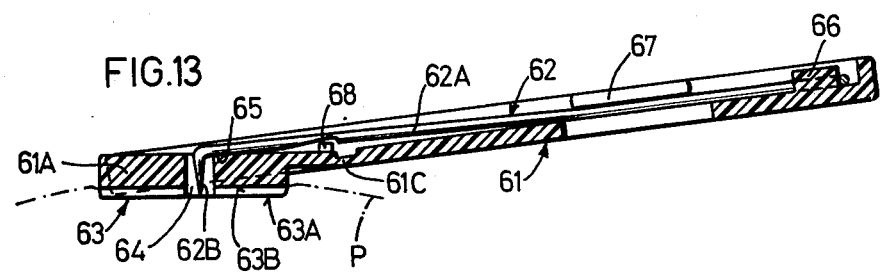

SKIN INCISING DEVICE

This is a continuation of application Ser. No. 132,409, filed Mar. 21, 1980, now abandoned, which is a continuation-in-part of application Ser. No. 945,099, filed Sept. 22, 1978 and now abandoned.

BACKGROUND OF THE INVENTION

1. Field of the Invention:

This invention relates to a device for making a skin incision of predetermined depth and predetermined length.

2. Prior Art:

Determination of a patient's bleeding time in accordance with the method devised by Ivy includes making a skin incision on the palm side of the patient's forearm and measuring the time that elapses until the bleeding has crease. On each occasion two such determinations are made with the incisions parallel and separated about 2 cm. The mean value of the measured bleeding times is taken.

In order that the determination may produce a correct result, the skin incision must have a certain standardized depth and it should also have a certain standardized length. In practice it is necessary therefore to use some form of mechanical device for making the incision.

Skin incision devices for use in the determination of bleeding time according to the method of Ivy are known in the art. Examples of known embodiments of such devices are shown in U.S. Pat. Nos. 3,712,293 and 3,902,475 and French Patent Publication No. 2,327,755. The prior art devices are disadvantageous in some respects, e.g. by being unhandy and/or expensive.

SUMMARY OF THE INVENTION

The general object of the present invention is to provide an improved skin incision device. A more specific object is to provide an inexpensive skin incising device which is simple to use and which reproducibly produces an incision having a predetermined, constant depth throughout the length thereof.

According to the invention, these and other objects are realized in a skin incising device constructed in accordance with the claims.

The device includes a guide which guides a cutter having a cutting tip. In a retracted position, the cutter is latched against biasing means, and on release of the latching means, the biasing means moves the cutting tip through a space of predetermined length and depth adapted to be disposed against the skin.

For a full understanding of the invention, three embodiments thereof are described with reference to the drawings.

BRIEF DESCRIPTION OF THE DRAWINGS

FIG. 1 is a perspective view of a first embodiment and shows the incising device in cocked position ready for use;

FIGS. 2 and 3 are views in longitudinal section respectively showing the incising device in cocked position and in the position it assumes after completed incision;

FIG. 4 is a cross-sectional view on line IV—IV of FIG. 2;

FIG. 5 is a perspective view of a second embodiment;

FIG. 6 is a view in longitudinal cross-section on line VI—VI of FIG. 5, showing the incising device in cocked position ready for use;

FIG. 7 corresponds to FIG. 6, showing the device in the position it assumes after a completed incision;

FIG. 8 is a cross-sectional view on line VIII—VIII of FIG. 6;

FIG. 9 is a plan view of a third embodiment and shows the incising device in cocked position ready for use;

FIG. 10 is an elevational view of the incising device shown in FIG. 9;

FIG. 11 is a cross-sectional view on line XI—XI of FIG. 9

FIG. 12 is a cross-sectional view on line XII—XII of FIG. 9; and

FIG. 13 is a sectional view on line XIII—XIII of FIG. 9 and illustrates releasing of the latching means.

DETAILED DESCRIPTION

The skin incising device shown in FIGS. 1 to 4 comprises three main elements: a tubular body or blade guide 11 which also forms a housing or case of the device, a cutter in the form of a blade assembly 12 which is axially displaceable in the blade guide, and a compression spring 13 acting between the blade guide and the blade assembly. The blade assembly 12 comprises two parts, a blade holder 14 and a flat steel blade 15 firmly held in a recess 16 of the blade holder. The blade guide 11 and the blade holder 14 are made of acetal plastic (Delrin, a registered trademark of E. I. Du Pont de Nemours and Company).

The blade guide 11 is generally cylindrical exteriorly and has a flat base surface 17 which is parallel to the blade guide axis and extends throughout the length of the blade guide. Approximately halfway between the ends of the blade guide the base surface 17 has an intermediate portion 17A which is offset towards the longitudinal axis of the blade guide a distance at least equal to the predetermined or desired depth of the incision to be made. The offset base surface portion 17A is parallel to the adjoining front and rear portions 17B, 17C of the base surface 17, and its length is approximately equal to the predetermined standardized or desired length of the skin incision.

A cylindrical bore 18, the axis of which is parallel to, but slightly spaced from, the axis of the cylindrical outer surface of the blade guide 17, extends from the front end 11A of the blade guide to the vicinity of the rear end 11B. A pair of lower and upper longitudinal slots 19 and 20 formed in a common plane perpendicular to the base surface 17 extend from the front end 11A of the blade guide 11. The lower slot 19 opens into the end portion 17C of said base surface 17. The upper slot 20 is slightly shorter. The slots are sufficiently wide to slidably accommodate the blade 15. Approximately halfway between the ends of the upper slot 20 the blade guide 17 also has a transverse slot 21.

The blade holder 14 comprises a slightly conical body the circular large end 25 of which faces the rear blade guide end 11B and forms an abutment for the spring 13. A cylindrical projection 26 on the large end 25 serves to keep the spring 13 in position. The small end of the blade holder body has a circular rim 27 the thickness of which is slightly smaller than the width of the transverse slot 21. Both the large end 25 and the rim 27 have a loose sliding fit with the straight guideway defined by the bore 18 of the blade guide 11 so that the blade holder body can readily be displaced axially along the guideway without any substantial radial play.

The flat blade 15 is wedged or secured in any other suitable manner to the blade holder 14 in a plane containing the axes of the blade holder and the blade guide 11. More particularly, when the blade holder 14 is inserted in the blade guide bore 18 as shown in FIG. 2, the tip 15A of the blade 15 is accommodated in the lower blade guide slot 19 and extends past the level of the intermediate base surface portion 17A a distance equal to the predetermined desired depth of the incision to be made. Since the intermediate base surface portion 17A is offset from the front and rear end portions 17B, 17C a distance at least equal to the just-mentioned distance, the tip portion 15A projects from the base surface 17 only when it is at the intermediate portion 17A. The upper end portion 15B of the blade 15 extends through the upper slot 20 and projects upwardly from the blade guide to form a finger grip.

The skin incising device of the invention can advantageously be produced as a disposable item. It is then supplied in a sterile package ready for use in the blade assembly 12 in the retracted and cocked position shown in FIG. 2. In this position the front portion of the blade assembly 12 is slightly lifted and the upper portion of the rim 27 is engaged in the transverse blade guide slot 21 with the compressed spring 13 urging the front face 27A of the rim against the front rearwardly facing wall 21A of the slot. The friction between the rim and the wall of the slot is sufficient to retain the blade assembly 12 in the retracted and cocked position during shipping and handling. As shown in FIG. 2, the tip 15A of the blade 15 is concealed in the portion of the lower blade guide slot 19 which extends into the rear end base surface portion 17C.

When a skin incision is to be made using the device shown in FIGS. 1 to 4 the nurse or other person making the incision grips the ends of the blade guide 11 between the thumb and the middle finger of one hand. The index finger is allowed to rest against the upper portion of the blade guide rearwardly of the upwardly projecting finger grip portion 15B of the blade 15. The base surface 17 of the blade guide 11 is engaged with the area of the patient's skin to be incised—typically the palm side of the forearm—and firmly pressed against the skin so that the skin is flattened against substantially the entire intermediate base surface portion 17A. In FIG. 2 the skin area to be incised is indicated at P. Using the index finger the nurse then presses against the upwardly projecting blade portion 15B, either forwardly as indicated by an arrow 30 or downwardly as indicated by an arrow 31. The finger pressure will cause the blade holder 14 to pivot about the large end 25 until the rim 27 clears the wall 21A of the slot 21. When the latch formed by the rim 27 and the slot wall 21A has thus been released, the compressed spring 13 displaces the blade holder 14 with the blade 15 to the advanced position shown in FIG. 3 in which the blade tip 15A, having traversed the intermediate base surface portion 17A, is concealed in the portion of the slot 19 opening into the front end base surface portion 17B. As the blade tip 15A traverses the intermediate base surface portion 17A it produces a skin incision the length of which is closely related to the length of the intermediate base surface portion 17A. For practical purposes the length of the skin incision may be considered to be equal to the length of the intermediate base surface portion; the exact length is dependent on the shape and dimensions of the transitions from the intermediate base surface portion to the front and rear base surface portions. The depth of the incision is constant throughout the length thereof and equal to the distance by which the blade tip 15A projects past the intermediate base surface portion 17A.

If two consecutive incisions are to be made on each patient as is common practice, the nurse may easily make the device ready for the second incision by gripping the upper blade portion 15B between the thumb and index finger and pulling it rearwardly toward the retracted position as indicated by an arrow 32 in FIG. 3 until the rim 27 snaps into the transverse slot 21 under the action of the turning moment about the large end 25 produced by the pulling force applied to the blade portion 15B.

The general structure and operation of the embodiment shown in FIGS. 5 to 8 is similar to the embodiments of FIGS. 1 to 4. The case or housing forming the blade guide 40 is made of acetal plastic (Delrin) and comprises two molded channel elements 40A, 40B held together by a pair of short transverse pegs 41 integral with the channel element 40A and inserted in recesses in the channel element 40B.

The channel element 40A has a longitudinal recess 42 the walls of which define a straight guideway for the blade assembly together with the adjacent flat face of the other channel element 40B.

The blade assembly 43 comprises a blade holder 44 of acetal plastic and a flat steel blade 45. The blade 45 is held in oblique position on the blade holder 44 by a pair of short pegs 46, 47 integral with the blade holder 44. The pegs 46 protrude through a pair of longitudinal slots 48A, 48B of the channel elements 40A, 40B so that the blade assembly 43 can be manipulated from outside the blade guide 40.

A compression spring 49 is interposed between the rear end of the blade holder 44 and a transverse rear wall of the recess 42.

Along its bottom portion the blade guide 40 has an elongated, generally flat cantilevered segment 50 which is separated from the body of the blade guide by a longitudinal slot 51 having a rounded rear or inner end 51A. The upper side 52 of the cantilevered segment 50 defines a portion of the straight guideway for the blade assembly 43, and its bottom side forms a base surface 53 comprising intermediate, front end, and rear end portions 53A, 53B, 53C, all of which are flat and generally parallel to each other and to the longitudinal axis of the guideway. The intermediate base surface portion 53A is offset from the front and rear end portions 53B, 53C toward the guideway a distance at least equal to the predetermined standardized or desired depth of the skin incision to be made and its length is approximately equal to the predetermined standardized or desired length of the incision.

A longitudinal vertical slot 54 through the cantilevered segment 50 extends throughout the intermediate base surface portion 53A and partly through the adjoining portions of the segment and slidably receives the tip 45A of the blade 45. The upper portion 45B of the blade is slidably received in a longitudinal slot 55 formed in the upper portion of the blade guide 40.

In the retracted and cocked position of the blade assembly 43 shown in FIG. 6, a transverse shoulder 44A on the lower side of the blade holder 44 abuts a confronting transverse face 56 on the blade guide 40 adjacent the free end of the cantilevered segment 50 under the action of the compressed spring 49. In this position, in which the blade assembly is thus latched against forward movement, the tip 45A of the blade 45 is concealed in the rear portion of the slot 54.

The latch formed by the shoulder 44A of the blade holder 44 and the transverse face 56 of the blade guide 40 can be released by displacing the cantilevered member 50 upwardly against the resistance produced by the friction between the shoulder 44A and the face 56 and by the resilience of the ligament 50A joining the cantilevered segment 50 to the body of the blade guide 40. In use of the incising device, such displacement is brought about by pressing the device against the patient's skin after the cantilevered segment 50 has been engaged with the skin area to be incised.

As soon as the front portion of the blade holder 44 has been displaced upwardly sufficiently for the shoulder 44A to clear the face 56, the spring 49 displaces the blade holder with the blade to the advanced position shown in FIG. 7. During its movement over or through the intermediate base surface portion 53A, the tip 45A of the blade 45 protrudes from the surface portion a distance equal to the predetermined standardized or desired depth of the incision to be made.

Since the blade holder latch 44A, 56 is released in response to exerting a predetermined pressure on the patient's skin through the cantilevered segment 50, the incising device of FIGS. 5 to 8 eliminates any errors in the bleeding time determinations which may be caused by varying pressure on the skin. The pressure required to release the latch is determined primarily by the force of the spring 49 and the resiliency of the ligament 50A, and since these parameters are fairly easy to control with sufficient accuracy during manufacture, the release pressure will not vary significantly from one device to the other.

The incising device shown in FIGS. 9 to 13 is the presently preferred embodiment of the invention. It only comprises two parts: a cutter guide or blade guide in the form of a generally plate-shaped body 61 integrally molded from acetal plastic, such as Delrin, and a cutter 62 which is supported by the body and formed by a bent length of spring wire.

The lower surface of the plate-shaped body 61 has, on the body portion 61A or segment that is to the left in FIGS. 9 and 10 and that is here regarded as the front body portion, a base surface 63 which is engageable with the area of a patient's skin where the incision is to be made. The base surface 63 comprises three substantially flat portions, two end portions 63A of relatively small extension laterally (up-down direction in FIG. 9 and left-right direction in FIG. 11) and an intermediate portion 63B bounded by the outer portions and having a length, i.e. lateral extension, corresponding to the desired length of the incision. The intermediate portion 63B is offset parallel to itself upwardly relative to the two coplanar outer end portions 63A by a distance almost the same as but slightly larger than the desired depth of the incision.

The front body portion or segment 61A is united with the rear body portion 61B by an integral resilient joint 61C enabling the front portion 61A and the rear portion or segment 61B to flex upwardly relatively to one another against the resilience of the joint 61C; the flexing takes place about a transverse axis 61H extending through the joint.

The front portion 61A of the body 61 has a slot 64 extending across the intermediate portion 63B of the base surface 63 and into the outer or end base surface portions 63A. The top face of the front body portion 61A is flat and parallel to the intermediate base surface portion 63B at least within the region that is situated directly rearwardly of the slot 64; this region of the top face forms a guideway for the cutter 62.

The cutter 62, which is made from spring wire of circular cross-section to serve also as a biasing means, is generally V-shaped and is secured to the body 61 near the rear or right-hand (as viewed in FIGS. 9 and 10) end of the body. One limb or blade holder 62A of the cutter extends forwardly along the top face 61F of the body. The front end of the limb 62A merges with a bent end portion 62B which is pointed to form a cutting tip or blade. The end portion 62B extends through the slot 64 substantially normal to the guideway 65 the base surface 63. The other limb 62C resiliently engages a lateral part of the body 61.

As best shown in FIG. 9, the cutter 62 extends about a circular upstanding projection 66 on the body 61 near the rear end thereof. More particularly, the cutter is arranged such that the limb 62A with the end portion 62B forming the cutting tip is pendulously movable relative to the body 61 about a point on or near the projection 66. Because of the illustrated mounting of the cutter 62, the limb 62A is biassed so as always to tend to move towards an advanced position which is indicated in dash-dot lines in FIG. 9. In addition, the limb 62A is biassed against the guideway 65 so that the limb tends to maintain the portion 62D thereof which is adjacent the end portion 62B in sliding engagement with the guideway. To this end, the body 61 is provided with a tongue 67 overlying the limb 62A and exerting a downward force on it. The tongue 67 and a similar tongue 67A also assist in retaining the cutter 62 in place on the body 61 so that no separate fastening elements are required to secure the cutter to the body.

When the cutter 62 is in the retracted, cocked position shown in full lines in FIG. 9 with the limb portion 62D in engagement with the guideway 65, the extreme end of the end portion 62B forming the cutting tip is slightly above the plane containing the outer end portions 63A of the base surface 63 and slightly below the plane containing the intermediate base surface portion 63B; the distance by which the end portion protrudes from the plane containing the intermediate base surface portion 63B is equal to the controlled depth of the incision to be made.

In order that the cutter 62 may be releasably retained in the retracted, cocked position shown in full lines in FIG. 9 against the action of the bias of the limb 62A tending to move the limb to the advanced position, releasable latching means are provided acting between the blade guide and the blade holder. To this end the top face of the front body portion 61A has an upstanding lug 68, the shape of which is best shown in FIG. 12. This lug 68 is positioned well behind the slot 64, namely, adjacent to the resilient joint 61C, see FIG. 9. The lug 68 has an end face 68A which is normal to the guideway 65 and forms a latching abutment for the cutter limb 62A. The limb is released by moving the limb 62A upwardly from the front body portion 61A in the region of the lug 68 until it is disengaged from the lug and thus allowed to move towards the advanced position under the action of its bias.

Finally, the body 61 is provided with a pair of forwardly directed arms 61D disposed on opposite sides of, and spaced from, the front body portion 61A and having finger grip projections 61E. As shown in FIG.

10, the bottom side of each arm is flush with the flat bottom face 61G of the rear body portion 61B, that is, slightly higher than the base surface 63.

The skin incising device of the invention can advantageously be produced as a disposable item. It is then supplied in a sterile package ready for use with the cutter 62 in the retracted, cocked position shown in FIG. 9. In this position, the cutting tip 62B is concealed in the end portion of the slot 64 extending into the lower (as viewed in FIG. 9) end portion 63A of the base surface 63, see also FIG. 11. Thus, the cutting tip is held away from the intermediate base surface portion 63B.

When a skin incision is to be made using the device shown in FIGS. 9 to 13, the nurse or other person making the incision grips the body 61 at the projections 61E between the thumb and index finger of one hand. The base surface 63 is engaged with the area of the patient's skin to be incised and firmly pressed against the skin so that the skin is flattened against substantially the entire intermediate base surface portion 63B. In FIGS. 11 and 13 the skin is indicated by a dash-dot line at P.

When the base surface 63 is pressed against the skin, the joint 61C will allow the front body portion 61A and the rear body portion 61B to flex upwardly relative to one another as shown in FIG. 13. As a consequence, the limb 62A will be lifted sufficiently from the top face 61F in the region of the latch lug 68 to clear the lug and move to the advanced position under the action of the bias. The limb portion 62D will slidably engage the flat area 65, namely, the region of the area 65 which is adjacent to the slot 64 and forms the aforesaid guideway, throughout the movement to the advanced position.

As the cutting tip 62B of the cutter traverses the intermediate portion 63B of the base surface 63, it protrudes from the intermediate base surface portion a distance equal to the desired depth of the incision. Thus, as the cutting tip 62B moves across the intermediate base surface portion 63B, it makes a skin incision the length of which corresponds to the length of the intermediate base surface portion and the depth of which is constant and equal to the distance by which the cutting tip 62B protrudes downwardly from the intermediate base surface portion 63B.

If two consecutive incisions are to be made on each patient, the nurse may make the device ready for the second incision by moving the cutter 62 back to the cocked position shown in FIG. 9 by a finger.

The cutter 62 preferably is made of round spring wire, and in order that the limb 62A, upon release of the latch formed by the lug 68, may not be thrown upwardly by camming action between the lug and the curved surface of the wire, the cross-section of the wire is modified in the region of the limb 62A which engages the lug. The modified cross-section is shown in FIG. 12 and may advantageously be produced by grinding. In practice, the grinding of the modified cross-section is effected simultaneously with the grinding of the cutting tip formed by the cutter end portion 62B.

As shown in FIG. 9, the slot 64 is arcuate, and because of the curvature of the cutter limb 62A and its pendulous movement from the retracted, cocked position to the advanced position, the incision will be curved. However, the curvature of the incision may be reduced by a suitable choice of the ratio of the length of the cutter limb to the length of the incision and a suitable choice of the shape of the slot. Besides, unless the curvature of the incision is very sharp, it has no significant adverse effect; the important points are that the length and depth are within the prescribed limits and that the depth is constant throughout the incision.

The invention is not limited to the embodiments specifically illustrated and described by way of example. It should be understood, therefore, that other embodiments may be considered as coming within the spirit and scope of the invention as defined by the claims. A feature common to such embodiments is that the cutter performs an incising movement at a controlled depth in parallel with the skin under the action of an accumulated force after a cutter latch has been released to allow the accumulated force to displace the cutter along a guideway.

We claim as our invention:

1. A device for making a skin incision of controlled length and uniform depth, comprising:
   (a) a blade guide defining a guideway, and having a base surface of a length exceeding the length of the incision for being engaged throughout its extent with a patient's skin, said base surface having a flat intermediate portion in which there is a slot of a length approximately equal to the controlled length and a pair of end portions respectively disposed at opposite ends of said flat intermediate portion, said intermediate portion being substantially parallel to said guideway and offset from said end portions of said base surface toward said guideway a distance at least equal to the uniform depth;
   (b) a blade holder supported by said blade guide, and movable relatively thereto along said guideway between a retracted and an advanced position;
   (c) a blade secured to said blade holder and having an incising tip at all times projecting into said slot, its free end being located adjacent to said base surface, said tip in the retracted and advanced positions of said blade holder being retracted from said base surface into said end portions of said base surface, and said tip, during movement of said blade holder from the retracted position to the advanced position, traversing said intermediate base surface portion and projecting therefrom a distance equal to the uniform depth;
   (d) means biasing said blade holder toward said advanced position; and
   (e) means on said guide and on said blade holder for latching said blade holder in said retracted position, said latching means being releasable by forcing said base surface against the skin to enable said biasing means to displace said tip to the advanced position.

2. A device according to claim 1, said slot extending entirely across said intermediate base surface portion and at least partly into said end portions of said base surface.

3. A device according to claim 1 or 2, said blade guide comprising a body portion and a segment which is resiliently displaceable relatively to said body portion in a direction normal to said intermediate portion of said base surface, said segment having said base surface portions thereon, said latching means being releasable in response to relative angular displacement of said blade guide body portion and said blade guide segment in said direction.

4. A device for making a skin incision of controlled length and uniform depth comprising:
   (a) a cutter guide having a base surface adapted to be pressed against the patient's skin, said base surface having a flat skin-engaging depression of a length for responding to the controlled length, there being a slot in said base surface extending across said depression; and (b) a resiliently biased cutter supported on and guided by said cutter guide and having a cutting tip projecting through said slot at said flat depression by a distance corresponding to said uniform depth, said cutting tip being in a non-projecting position at both ends of said slot, said cutter being guided to move parallel to the skin in said depression from a releasably latched retracted position at one end of said slot under the force of its bias to an advanced position at the opposite end of said slot, the force of said base surface against the skin effecting such release.

5. A device for making a skin incision of controlled length and uniform depth, comprising:
(a) a molded one-piece plastic body having a flat base surface adapted to be engaged with a patient's skin, and a flat cutter guideway extending substantially parallel to the base surface;
(b) a wire spring having a pointed cutting tip extending substantially perpendicularly to said base surface and a limb section secured to said cutting tip and slidably engaging exclusively said cutter guideway, said spring being secured to and supported by the configuration of said body remotely from said limb section, said cutting tip and said limb section being moveable relatively to said body from a retracted position, to an advanced position toward which they are resiliently biased, said cutting tip protruding a constant distance from said base surface equal to said uniform depth when said cutting tip is moved between said retracted and advanced positions, and
(c) means for latching said limb in said retracted position, said means being releasable by forcing said base surface against the skin to permit the cutter to move from said retracted position to said advanced position under the action of bias in said spring.

6. A device according to claim 5, said body having upper and lower surfaces, said spring being secured to said body adjacent to one end of said body, said spring extending along said upper face of said body, and said flat skin-engaging base surface being disposed on the lower face of said body.

7. A device according to claim 6, said latch means comprising a molded projection on said upper face of said body, said projection having an abutment face having a height at least equal to the cross-section of said wire spring and engageable with said limb section of said wire spring.

8. A device according to claim 7, said projection being disposed at a distance from said cutter tip, and said latch means being releasable by bending said molded body about an axis enabled by a line of reduced thickness located parallel to the plane of said guideway adjacent to said projection.

9. A device according to claim 5, said base surface comprising a flat intermediate portion of a length approximately equal to said controlled length, and end portions disposed at opposite ends of said intermediate portion, said flat intermediate portion being slightly recessed from said end portions towards said guideway by a distance at least equal to said uniform depth.

10. A device according to claim 9, said body having a slot in which said cutting tip is always disposed, said slot extending across said intermediate base surface portion through which said cutting tip extends, and into both of said end portions of said base surface, whereby the cutting tip is spaced from skin engaging said base surface end portions.

* * * * *